(12) United States Patent
Tanger et al.

(10) Patent No.: US 6,630,608 B2
(45) Date of Patent: Oct. 7, 2003

(54) PROCESS FOR PREPARING PHENOLS

(75) Inventors: Uwe Tanger, Bochum (DE); Reinhard Sigg, Marl (DE); Siegmund Greschek, Gladbeck (DE); Manfred Weber, Haltern (DE)

(73) Assignee: INEOS Phenol & GmbH Co., KG, Gladbeck (DE)

( * ) Notice: Subject to any disclaimer, the term of this patent is extended or adjusted under 35 U.S.C. 154(b) by 36 days.

(21) Appl. No.: 10/090,475

(22) Filed: Mar. 4, 2002

(65) Prior Publication Data

US 2002/0183563 A1 Dec. 5, 2002

(30) Foreign Application Priority Data

Mar. 3, 2001 (DE) .......................................... 101 10 392

(51) Int. Cl.$^7$ .............................................. C07C 37/68
(52) U.S. Cl. ........................ 568/754; 568/385; 568/798
(58) Field of Search ................................. 568/754, 798, 568/385

(56) References Cited

U.S. PATENT DOCUMENTS

| | | | | |
|---|---|---|---|---|
| 3,862,244 A | * | 1/1975 | Genod | |
| 3,931,339 A | * | 1/1976 | Cooke | |
| 4,016,213 A | * | 4/1977 | Yeh | |
| 4,358,618 A | | 11/1982 | Sifniades et al. | |
| 5,003,109 A | * | 3/1991 | Costantini | |
| 5,414,151 A | * | 5/1995 | Pressman | |
| 5,475,157 A | * | 12/1995 | Araki | |
| 6,066,767 A | * | 5/2000 | Zakoshansky. | |

FOREIGN PATENT DOCUMENTS

DE     100 21 482     8/2001

* cited by examiner

*Primary Examiner*—Michael L. Shippen
(74) *Attorney, Agent, or Firm*—Knobbe, Martens, Olson & Bear, LLP

(57) ABSTRACT

The present invention relates to a process for preparing phenols, in which the pH of the reaction product from the acid-catalyzed cleavage of alkylaryl hydroperoxides is set to a value of at least 8 at a temperature of at least 100° C. prior to the work-up of the product. This measure enables the content of undesirable by-products, e.g. hydroxyacetone, in the cleavage product to be significantly reduced. This procedure is particularly advantageously integrated into a process for preparing phenols by:

a) acid-catalyzed cleavage of alkylaryl hydroperoxides and b) thermal after-treatment of the cleavage product from step a), with the temperature in step b) being higher than in step a) and is at least 100° C., wherein the adjustment to a pH of at least 8 is carried out after the thermal after-treatment and prior to cooling of the cleavage product.

17 Claims, 3 Drawing Sheets

PROCESS FOR PREPARING PHENOLS

This is the U.S. application that claims priority to the German Application 101 10 392.1, filed Mar. 3, 2001.

BACKGROUND OF THE INVENTION

1. Field of the Invention

The present invention relates to an improved process for preparing phenols.

2. Description of the Related Art

The process of acid-catalyzed cleavage of cumene hydroperoxide into phenol and acetone has been of particular industrial importance for a long time. In the preparation of phenol from cumene by the Hock process, cumene is oxidized to cumene hydroperoxide (CHP) in a first reaction step, known as oxidation, and the CHP is subsequently concentrated to from 65 to 90% by weight in a vacuum distillation, known as concentration. In a second reaction step, known as cleavage, the CHP is cleaved into phenol and acetone by action of an acid, usually sulfuric acid. In this step, the dimethyl phenyl carbinol (DMPC) formed in the oxidation is partly cleaved in an equilibrium reaction into α-methylstyrene (AMS) and water, while a further part of the DMPC reacts with CHP to form dicumyl peroxide (DCP); the rest remains in the cleavage product. After neutralization of the cleavage product, this product mixture is usually worked up by distillation.

In the cleavage, part of the AMS or of the DMPC forms high boilers (dimers, cumylphenols, bisphenols) which are discharged as residue in the distillation. The AMS still present after the neutralization, is hydrogenated to cumene in the distillation and is returned to the oxidation. DMPC which is not reacted in the cleavage ends up as high boiler in the residue; part of it reacts further in the hot phenol columns from which high-boiling secondary components are once again formed. DCP is stable at customary cleavage temperatures (50° C.–70° C.). It decomposes thermally in the hot phenol columns forming, in our experience, o-cresol, at least in part. On the other hand, in the presence of acid, DCP can be cleaved into phenol, acetone and AMS at temperatures above 80° C. It is therefore obvious for the remaining DMPC and the DCP formed in the cleavage to be reacted completely immediately after the cleavage by means of a targeted increase in the temperature in the presence of the acid used as catalyst in the cleavage. In this way, DMPC is largely converted into AMS and DCP is converted virtually completely into phenol, acetone and likewise AMS.

Such a thermal after-treatment of the cleavage product has already been described in U.S. Pat. No. 2,757,209, where temperatures above 100° C., specifically from 110° C. to 120° C., were employed. The objective of this thermal after-treatment was the complete dehydration of DMPC to AMS. On the other hand, U.S. Pat. No. 4,358,618 describes a thermal after-treatment which has the aim of converting all of the DCP formed in the cleavage into phenol, acetone and AMS; in that patent, temperatures of 120° C. and 150° C. are employed. U.S. Pat. No. 5,254,751 describes a thermal after-treatment which has the same objective as that in U.S. Pat. No. 4,358,618 and uses temperatures of from 80° C. to 110° C. Finally, in DE 197 55 026 A1, the after-treatment is carried out in a temperature range above 150° C. In all these processes known from the prior art, the thermally treated product is subsequently cooled to (customarily) 40° C. by means of a cooler, then neutralized and, after separating off a salt-containing aqueous phase, worked up by distillation.

A disadvantage of the above-described processes is that hydroxyacetone and other carbonyl compounds such as acetaldehyde are formed as by-products and these, firstly, make the work-up of the reaction product difficult and, secondly, hydroxyacetone in particular reacts with phenol in specific phenol purification processes to form high boilers, thus leading to undesirable losses of phenol. It would therefore be desirable to reduce the content of hydroxyacetone and other impurities in the cleavage product.

U.S. Pat. No. 6,066,767 describes a process for removing hydroxyacetone and other carbonyl compounds from the product of the cleavage of cumene hydroperoxide. For this purpose, the reaction product of the cumene hydroperoxide cleavage is extracted with an aqueous salt solution in a temperature range of 15°–80° C. to remove hydroxyacetone, inter alia. The loaded extractant is subsequently treated with a base in a separate reactor to convert hydroxyacetone into condensation products. The extractant which has been treated in this way is returned to the extraction stage where the condensation products go into the organic phase and are then separated off in the work-up of the phenol- and acetone-containing organic phase. The examples show that, despite the very complicated apparatus employed for purification by extraction and subsequent reaction of the extracted hydroxyacetone, the organic product phase which is passed to further work-up for the isolation of phenol still contains 500–800 ppm of hydroxyacetone.

SUMMARY OF THE INVENTION

It is therefore an object of the invention to provide a process for preparing phenols in which a reduction in the amount of undesirable impurities, in particular hydroxyacetone, prior to the work-up of the product can be achieved in a simple manner.

This object has been achieved by a process for preparing phenols, in which the pH of the reaction product from the acid-catalyzed cleavage of alkylaryl hydroperoxides is set to a value of at least 8 at a temperature of at least 100° C. prior to the work-up of the product.

It has surprisingly been found that this simple procedure leads to a drastically reduced content of undesirable by-products, in particular hydroxyacetone, without the complicated apparatus described in the prior art cited being necessary.

DETAILED DESCRIPTION OF THE PREFERRED EMBODIMENT

Figure 1:
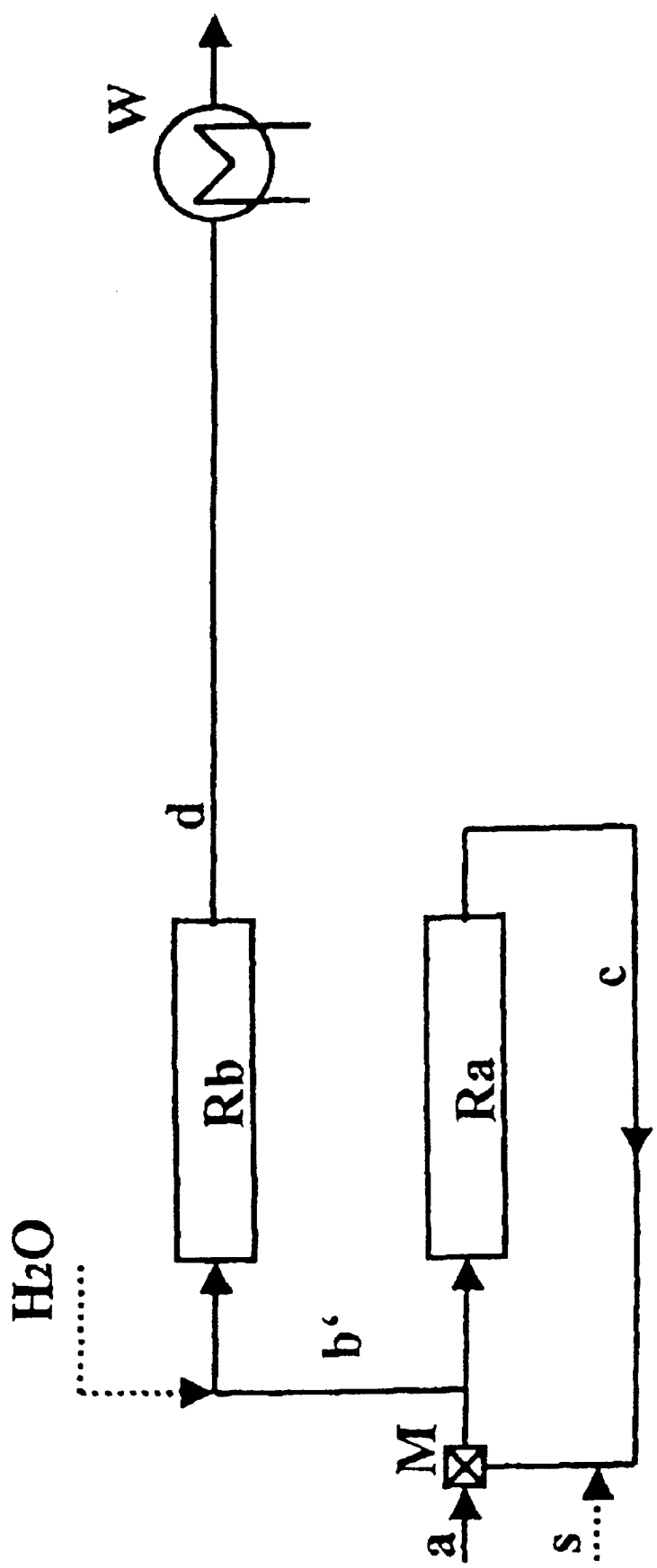
FIG. 1 shows a schematic flow diagram of the process described in DE-A10051081, which heat treatment is integrated into the high-temperature cleavage. A concentrate comprising the CHP to be cleaved is introduced via line a and mixed in a mixer M with the cleavage product c from the reactor Ra to form a mixture. When a homogeneous catalyst is used, this can be added to the cleavage product c via line s. Part of the mixture from the mixer M is fed into a first reactor Ra, namely the low-temperature cleavage reactor. The low-temperature cleavage reactor Ra does not have to be only one reactor which can, for example, be configured as a tube reactor with recirculation or as a backmix apparatus, but can also be made up of a plurality of reactors connected in series. The low-temperature cleavage product leaving the low-temperature cleavage reactor is, in the case of a tube reactor, recirculated via line c via the mixer M back to the low-temperature cleavage reactor. Before the mixture enters the reactor Ra, part of it is conveyed via line b' to a second cleavage reactor Rb namely the high-temperature cleavage reactor in which the high-temperature thermal cleavage takes place. Water ($H_2O$) can optionally be introduced via a line into the substream of the mixture upstream of the reactor Rb. The high-temperature cleavage product leaves the reactor Rb via line d and can be passed to work-up. Heat can be removed from the high-temperature cleavage product by means of the heat exchanger W.
Figure 2:
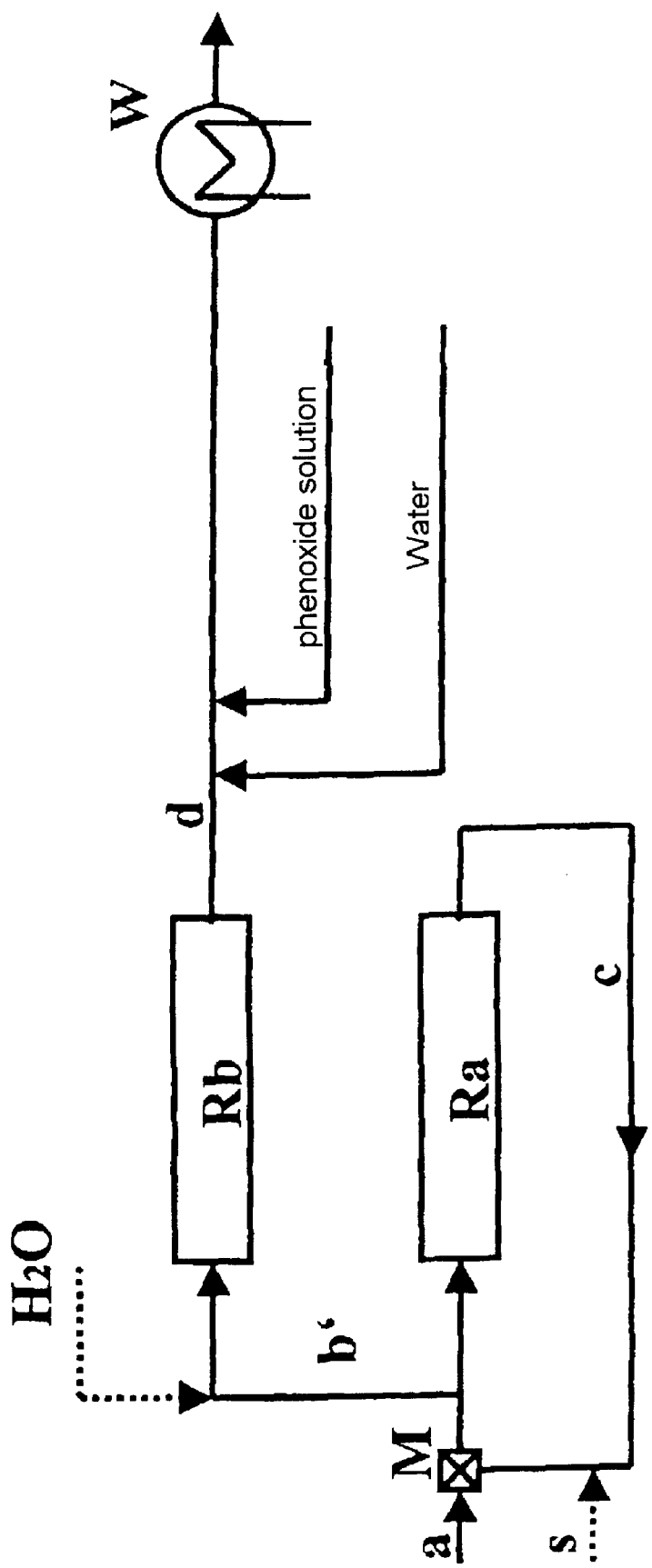
FIG. 2 shows an apparatus for carrying out the process of the invention. The apparatus differs from that described in FIG. 1 in that it is additionally provided with facilities for feeding water and a base, preferably phenoxide solution, into the line d immediately downstream of the outlet from the high-temperature cleavage reactor. This ensures that the cleavage product is saturated with water and set to the pH required according to the invention at the temperature of at least 100° C. at which it leaves the high-temperature cleavage reactor. After the pH has been set to the appropriate value, heat can be removed from the cleavage product by means of the heat exchanger W.

The process of the invention can be integrated particularly advantageously into processes known hitherto for preparing phenols by a) acid-catalyzed cleavage of alkylaryl hydroperoxides and b) thermal after-treatment of the cleavage product from step a), with the temperature in step b) being higher than in step a), since here the reaction product of the alkylaryl hydroperoxide cleavage is generally obtained at the required temperature of at least 100° C. and setting of the pH can be carried out in a simple manner prior to the otherwise customary cooling to about 40° C.

The process of the invention is suitable for the acid-catalyzed cleavage of one or more alkylaryl hydroperoxides (AAHPs), e.g. α-methylbenzene hydroperoxide, α-methyl-p-methylbenzyl hydroperoxide, α,α-dimethylbenzyl hydroperoxide, also known as isopropenylbenzene hydroperoxide or cumene hydroperoxide (CHP), α,α-methylethylbenzyl hydroperoxide, also known as sec-butylbenzene hydroperoxide, α,α-dimethyl-p-methylbenzyl hydroperoxide, αα-dimethyl-p-ethylbenzyl hydroperoxide, α-methyl-α-phenylbenzyl hydroperoxide. The process of the invention is particularly useful for the acid-catalyzed cleavage of mixtures of alkylaryl hydroperoxides comprising at least cumene hydroperoxide (CHP). The process of the invention is very particularly preferably used for the cleavage of CHP.

In the following, the process of the invention will be described by way of example for the case of the acid-catalyzed cleavage of CHP into phenol and acetone, without the process of the invention being restricted to this embodiment.

DE-A 100 21 482 discloses a process for preparing phenol by a) acid-catalyzed cleavage of cumene hydroperoxide and b) thermal after-treatment of the cleavage product from step a), with the temperature in step b) being higher than in step a), in which the heat of reaction of at least one exothermic reaction proceeding in the reactor is utilized for heating the cleavage product from step a) to be treated thermally in step b) in this reactor. The exothermic reaction is preferably the acid-catalyzed cleavage of cumene hydroperoxide. This process can readily be modified, as described above, in accordance with the present invention.

This procedure has the advantage that, compared to conventional processes, significantly less steam is required for heating the cleavage product. When the quantity of heat liberated in the reaction is sufficient for the thermal after-treatment of the cleavage product, the use of steam for heating the cleavage product can be dispensed with entirely. In contrast to processes or apparatuses in which steam or other suitable heat transfer media are used continually for heating the cleavage product, fouling of heat exchange apparatuses occurs to a substantially lesser extent, if at all.

The thermal after-treatment of cleavage product obtained in the acid-catalyzed cleavage of cumene hydroperoxide into phenol and acetone has the purpose of reducing the proportion of dimethyl phenyl carbinol (DMPC) and dicumyl peroxide (DCP) in the cleavage product, since these compounds react further during the subsequent work-up of the cleavage product, in which a plurality of distillation steps for separating materials are carried out, with other compounds or with themselves to form high-boiling, tar-like compounds. These high-boiling compounds can interfere in the further process steps for working up the cleavage product. In addition, the formation of the high boilers significantly reduces the yield in the overall Hock phenol synthesis.

In the thermal treatment or after-treatment of the cleavage product, the DMPC present therein is cleaved into α-methylstyrene (AMS) and water and the DCP which is likewise present is cleaved into phenol, AMS and acetone. The AMS formed in these reactions can be separated off from the cleavage product during its further work-up and be hydrogenated to give cumene, which can be recirculated as starting material to the beginning of the overall phenol production process. In this way, the yield losses caused by the formation of by-products are reduced.

For the abovementioned reasons, the cleavage product which is to be subjected to thermal after-treatment is heated to a temperature above 100° C., preferably above 115° C. This thermal after-treatment is also known as heat treatment. The cleavage product is thus already at the temperature necessary for the setting of the pH according to the invention.

For the thermal after-treatment of the cleavage product, the latter is transferred to reactor, preferably a tube reactor, and heated. The heating of the cleavage product mixture is carried out by utilizing the heat of reaction which is evolved in the cleavage product as a result of at least one exothermic reaction. One of the exothermic reactions is preferably the acid-catalyzed cleavage of CHP. Since the cleavage product is heated directly utilizing the heat of reaction of an exothermic reaction, indirect introduction of heat by means of heat transfer media to heat the cleavage product may be able to be dispensed with entirely.

The cleavage of DMPC into AMS and water and especially the cleavage of DCP into phenol, acetone and AMS are likewise exothermic reactions and also liberate heat of reaction which corresponds to a defined increase in the temperature of the cleavage product. This temperature difference is, depending on the initial DMPC and DCP contents, usually from 10° C. to 20° C. Typical DMPC concentrations are from 0.5 to 2% by weight. Typical DCP concentrations are in the range from 2 to 6% by weight.

The quantity of heat liberated as a result of these abovementioned exothermic reactions has to be taken into account in calculating the initial CHP concentration in the cleavage product prior to the thermal after-treatment which is necessary to heat the cleavage product to the desired temperature.

As a starting point for calculating the initial CHP concentration necessary, it is possible to employ the rule of thumb which states that the cleavage of a 1% strength by weight CHP solution liberates approximately that quantity of heat which is necessary for increasing the temperature of the solution by 6.8° C.–7.0° C. Thus, a 6% strength by weight CHP solution would be heated by 40.8° C.–42° C. as a result of cleavage of all of the CHP. The rule of thumb is applicable to the solutions customarily used in the CHP cleavage. These usually comprise least cumene, phenol and acetone but only small amounts (from 0 to 15% by weight) of water. Owing to the higher heat capacity of water, the cleavage of CHP in a solution or dispersion comprising 99% by weight of water and 1% by weight of CHP would increase the temperature of this solution by only 3.5° C. For this reason, the heating factor has to be determined afresh for cleavage mixtures which contain a higher proportion of water than usual. This determination can be carried out in a manner known to those skilled in the art by means of simple preliminary tests.

The additional CHP necessary for producing the heat is, if it is not yet present in sufficient quantity in the cleavage product mixture, advantageously added afterwards to the cleavage product.

Sulfuric acid is preferably used as catalyst for the cleavage of CHP. The cleavage product mixture preferably has sulfuric acid concentration of from 50 to 1000 wppm. It can be advantageous to alter the acid activity, i.e. the acid strength of the cleavage product, prior to the thermal treatment. The acid strength is dependent on the acid concentration and the concentration of water in the cleavage mixture. The higher the water content of the cleavage mixture, the more acid has to be added to the cleavage mixture to obtain the same acid activity, with the acid strength being inversely proportional to the square of the water concentration. Thus, for example, the acid strength of a cleavage mixture solution containing 200 wppm of sulfuric acid and 2% by weight of water is only one sixteenth of the acid strength of a cleavage mixture solution containing 200 wppm of sulfuric acid and 0.5% by weight of water.

The ideal acid strength and thus the ideal composition of the cleavage mixture in respect of acid concentration and water concentration can be determined by means of simple preliminary tests. In the case of cleavage mixtures having a water concentration of up to 6% by weight, a sulfuric acid concentration of from 100 to 500 wppm in the cleavage mixture has been found to be particularly advantageous. To increase the acid strength, it is usual to add further sulfuric acid. To reduce the acid strength, it is possible to add a base, e.g. a phenoxide solution, ammonia or sodium hydroxide solution, or water to the cleavage product. Preference is given to adding water to the cleavage product.

In a particularly preferred embodiment of the process of the invention, the cleavage product to be treated thermally has a CHP concentration which in combination with the concentrations of further compounds which react exothermically during the cleavage reaction liberates precisely that quantity of heat which will heat the cleavage product mixture to the desired temperature for the thermal after-treatment.

All the embodiments described in DE-A 100 21 482 and the reactors suitable for them can likewise be used in the process of the present invention.

As an alternative, it is also possible, using a procedure analogous to that described in DE-A 100 51 581, to produce a mixture of a cleavage product from step a) and a concentrate comprising at least cumene hydroperoxide, dividing this mixture into at least two parts and feeding at least one of these parts to the acid-catalyzed cleavage of step a) and subjecting another of these parts to a thermal after-treatment according to step b) and setting the pH of the reaction product from step b) in accordance with the invention.

The at least two parts of the mixture are preferably treated so that one part is treated at a temperature of from 45° C. to 99° C., preferably from 45° C. to 90° C., to bring about the cleavage of cumene hydroperoxide and another part is heated to temperatures above 100° C. to effect cleavage of cumene hydroperoxide. In the case of the part which is heated to temperatures above 100° C., cleavage of cumene hydroperoxide takes place together with an integrated thermal after-treatment. This part is preferably treated at a temperature above 115° C., particularly preferably above 130° C. and very particularly preferably above 150° C., with this temperature resulting from the exothermic reaction occurring in this step.

The precise setting of the composition of the mixture which is subjected to the high-temperature cleavage or the thermal after-treatment in order to obtain a desired temperature is described in detail in DE-A 100 51 581. The relevant disclosure of that patent publication is hereby incorporated by reference. Furthermore, all embodiments described in DE-A 100 51 581 and the reactors suitable for them can also be used in the process of the present invention.

In a preferred embodiment of the process of the invention, the pH of the product from the cumene hydroperoxide cleavage is set to a value of greater than 9, preferably greater than 10, particularly preferably greater than 11, in particular in the range 9–13, preferably 10–12. Within these preferred ranges, a particularly strong decrease in the hydroxyacetone content of the cleavage product is observed. The pH adjustment can be effected by mixing a base into the cleavage product by means of suitable apparatuses, e.g. one or more static mixers.

The pH adjustment is advantageously carried out using a base selected from among aqueous NaOH and aqueous phenoxide solution. Aqueous phenoxide solution is particularly useful for this purpose, since it is obtained anyway in the process for preparing phenol and can be conveniently recirculated in this way.

The preferred temperature range for the pH adjustment according to the present invention, particularly when the method of present invention is integrated into the process with thermal after-treatment of the cleavage product, is 100° C.–160° C., preferably 110° C.–150° C.

Since salts are formed during the pH adjustment by neutralization of the acid required for the cleavage reaction, it can be advantageous, depending on the reaction conditions, to saturate the cleavage product with water prior to the pH adjustment. In this way, the precipitation of salts or the deposition of salt crusts on equipment items can be avoided. This measure enables the process of the invention to be operated particularly economically, since dead times for removal of salt deposits from the plant can be largely avoided.

It is assumed, without being tied to a theory, that the hydroxyacetone formed in the cleavage reaction reacts in the temperature and pH range according to the invention to form condensation products which can easily be separated off from the product mixture. Furthermore, the pH adjustment immediately after the heat treatment suppresses acid-catalyzed secondary reactions, including the reaction of hydroxyacetone with phenol, which lead to yield losses of phenol and can continue to take place during the cooling phase. The process of the invention thus leads, in a simple manner, both to simplified removal of by-products and to an improvement in the selectivity, since hydroxyacetone is removed by reaction from the cleavage product and at the same time the undesirable reaction of hydroxyacetone with phenol, inter alia, is suppressed.

To enable the process of the invention, in particular the removal of hydroxyacetone from the cleavage product by reaction of the hydroxyacetone to form condensation products, to be controlled more readily, it can be advantageous to introduce the cleavage product into a residence time vessel after the pH adjustment and prior to cooling. Depending on the temperature chosen, a residence time in the range 10–3600 seconds can be set, with the residence time decreasing with increasing temperature of the cleavage product. To ensure optimum mass transfer, it is advantageous for the aqueous phase to remain dispersed in the organic cleavage product phase in the residence time vessel. This can be achieved by means of a suitable hydrodynamic configuration of the residence time vessel, as is known per se to a person skilled in the art. Thus, for example, an upright cylindrical apparatus can be equipped with separation plates by means of which the two-phase mixture flowing from the bottom upward is continually deflected, thus countering demixing. It is also possible to use a parallel or series arrangement of a plurality of apparatuses whose contents are circulated by pumping through a circulation line installed on each apparatus, so that demixing is avoided.

The process of the invention makes it possible to obtain a mixture comprising phenol and acetone in which the hydroxyacetone content does not exceed 400 wppm, preferably 300 wppm, particularly preferably 200 wppm and very particularly preferably 100 wppm.

The cleavage product is cooled after the pH adjustment according to the invention, then neutralized and fractionated. These steps are known per se to a person skilled in the are and are not critical to the present invention, so that a more precise description is not necessary.

The merits of the process of the invention are illustrated by the examples

COMPARATIVE EXAMPLE

In an apparatus as shown in FIG. 1, a cleavage product was produced from 68% strength by weight cumene hydroperoxide. The apparatus was operated so that the cleavage product has a water content of 1% by weight and a temperature of 120° C. on leaving the high-temperature cleavage reactor. The cleavage product was cooled to 40° C. and subsequently neutralized (pH=7). The hydroxyacetone content of the cleavage product was 1200 wppm.

EXAMPLE 1

Figure 3:
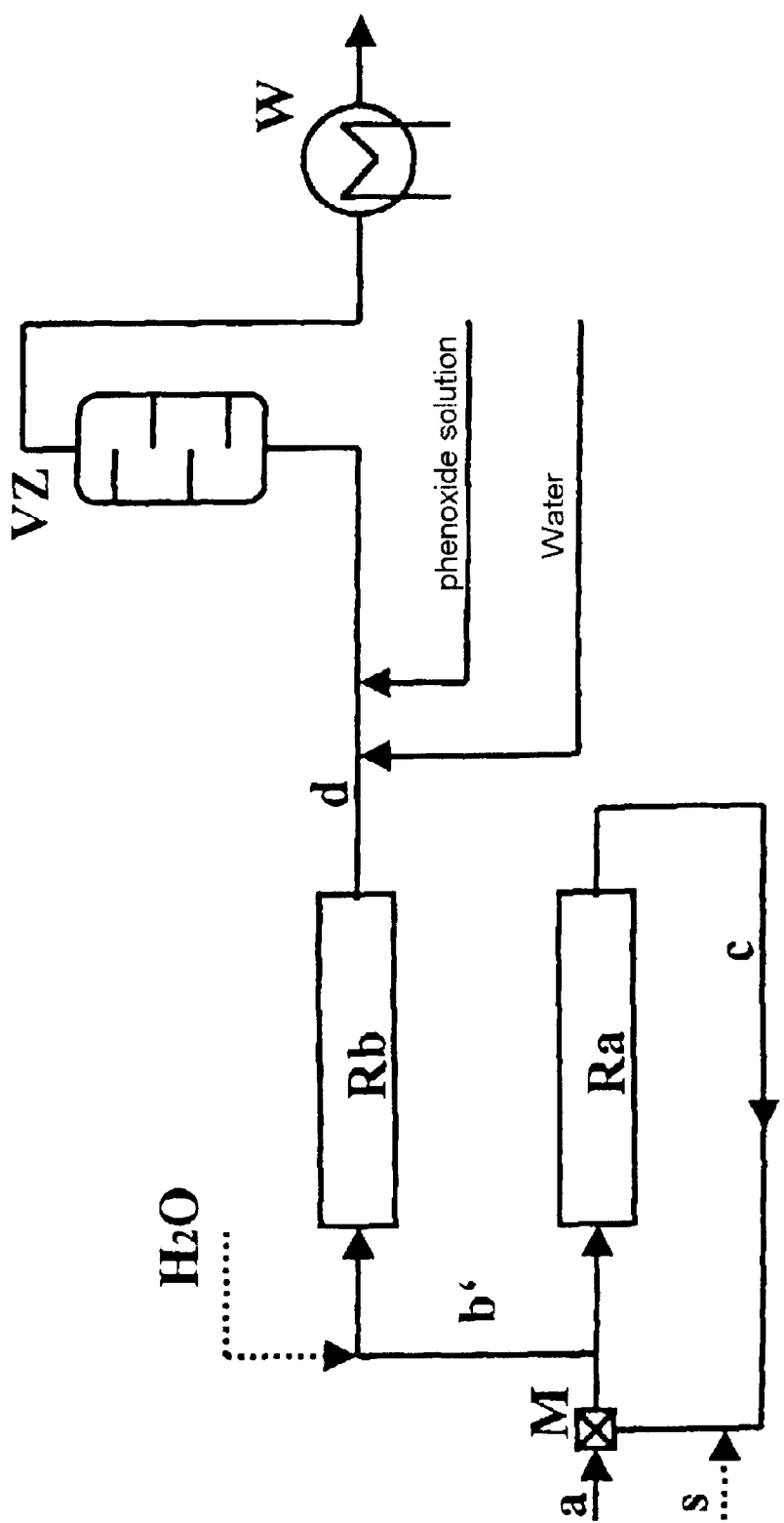
FIG. 3 shows a preferred apparatus for carrying out the process of the invention, in which a residence time vessel VZ is additionally installed between the facilities for introducing water and base and the heat exchanger W.

The comparative example was repeated with the difference that the cleavage was carried out using an apparatus as shown in FIG. 3. The cleavage product was saturated with water to a water content of 8% by weight and then brought to a pH of 10.5 by addition of a phenoxide solution prepared from 10% strength by weight NaOH immediately after leaving the high-temperature cleavage reactor. After a residence time of 10 minutes, the cleavage product was cooled to 40° C. and subsequently neutralized (pH=7). The hydroxyacetone content of the cleavage product was 360 wppm.

EXAMPLE 2

Example 1 was repeated with the difference that the cleavage product was brought to a pH of 11.0 by addition of a phenoxide solution prepared from 20% strength by weight NaOH. The hydroxyacetone content of the cleavage product was 30 wppm.

Comparison of the examples according to the invention and the comparative example showed that the hydroxyacetone content of the cleavage product was be significantly reduced by means of comparatively simple measures. This not only simplified the subsequent work-up but also increased the product selectivity. Even in comparison with the teachings of U.S. Pat. No. 6,066,767 (Example 4), in which complicated apparatus is required to reduce the hydroxyacetone content from 1300 wppm to 500 wppm, a significantly greater decrease in the hydroxyacetone content can be achieved when using the process of the present invention.

What is claimed is:

1. A process for preparing phenols, wherein a hydroxyacetone by-product is removed from a reaction product of acid-catalyzed cleavage of alkylaryl hydroperoxides by adjusting the pH of said reaction product to a value of at least 9 at a temperature of at least 100° C. prior to work-up of said reaction product by distillation.

2. A process for preparing phenols comprising the steps of:
   performing an acid-catalyzed cleavage of alkylaryl hydroperoxides to form a cleavage product;
   removing hydroxyacetone by-product from said cleavage product by:
      performing a thermal after-treatment of said cleavage product in a reactor, wherein the temperature is higher than in step (a) and is at least 100° C. to form a reaction product;
      adjusting the pH of the reaction product from step (b) to a pH of at least 9; and
      cooling the pH adjusted reaction product.

3. The process of claim 2, wherein the heat of at least one exothermic reaction occurring in the reactor is utilized for heating the cleavage product from step (a) which is to be thermally treated in step (b) in the reactor.

4. The process of claim 3, wherein said exothermic reaction occurring in the reactor in step (b) is the acid-catalyzed cleavage of alkyl hydroperoxides.

5. The process of claim 4, wherein a mixture of a concentrate comprising at least one alkyl hydroperoxide to be cleaved and the cleavage product from step (a) is produced, said mixture is divided into at least two parts, and at least one of these parts is subjected to the acid-catalyzed cleavage of step (a) and another of these parts is subjected to the thermal after-treatment of step (b).

6. The process of claim 2, wherein said pH is set to a value in the range of about 10 to about 13.

7. The process of claim 2, wherein said pH is set to a value in the range of about 10 to about 12.

8. The process of claim 2, wherein the adjustment of the pH is carried out using a base selected from the group consisting of aqueous NaOH and aqueous phenoxide solutions.

9. The process of claim 8, wherein the adjustment of the pH is carried out using a phenoxide solution.

10. The process of claim 2, wherein the temperature at which adjustment of the pH is carried out is from about 100° C. to about 160° C.

11. The process of claim 2, wherein the temperature at which adjustment of the pH is carried out is from about 110° C. to about 150° C.

12. The process of claim 2, wherein the reaction product of step (b) is saturated with water prior to adjustment of the pH.

13. The process of claim 12, wherein the reaction product of step (b) is conveyed into a residence time vessel after adjustment of the pH and prior to cooling.

14. The process of claim 13, wherein the residence time is from about 10 to about 3600 seconds.

15. The process of claim 13, wherein the product of step (b) has an aqueous phase and an organic phase and the aqueous phase remains dispersed in the organic phase in the residence time vessel.

16. The process of claim 2, wherein said alkylaryl hydroperoxide is cumene hydroperoxide.

17. The process of claim 2, further comprising the steps of neutralizing and fractionating the reaction product subsequent to cooling.

* * * * *

UNITED STATES PATENT AND TRADEMARK OFFICE
CERTIFICATE OF CORRECTION

PATENT NO. : 6,630,608 B2
DATED : October 7, 2003
INVENTOR(S) : Tanger et al.

It is certified that error appears in the above-identified patent and that said Letters Patent is hereby corrected as shown below:

Title page,
Item [73], Assignee, please change "INEOS Phenol & GmbH Co., KG" to
-- INEOS Phenol GmbH & Co. KG --
Item [57], ABSTRACT,
Line 13, please change "… with the temperature in step b) being higher than in step a) and is at least 100°C.," to -- with the temperature in step b) being than in step a) and being at least 100°C., --

Column 2,
Line 66, please add -- , -- after "…Rb"

Column 3,
Line 44, please change "isopropenylbenzene" to -- isopropylbenzene --
Line 48, please change "αα" to -- α,α --

Column 4,
Line 40, please insert -- a -- before "…thermal"
Line 47, please insert -- a -- before "reactor, preferably…"

Column 7,
Line 38, please change "…skilled in the are…" to -- …skilled in the *art*… --
Line 42, please add -- below -- after "examples"

Column 8,
Line 27, please insert -- (a) -- before "performing…"
Line 29, please insert -- (b) -- before "removing…"
Line 37, please insert -- (c) -- before "cooling…"

Signed and Sealed this

Eighteenth Day of May, 2004

JON W. DUDAS
*Acting Director of the United States Patent and Trademark Office*